United States Patent
Ward (10) Patent No.: US 9,868,963 B2
(45) Date of Patent: Jan. 16, 2018

(54) METHODS AND SYSTEMS FOR PRODUCTION OF ORGANICALLY DERIVED AMMONIA/AMMONIUM

(71) Applicant: CLEMSON UNIVERSITY RESEARCH FOUNDATION, Clemson, SC (US)

(72) Inventor: Brian Keith Ward, Charleston, SC (US)

(73) Assignee: Clemson University, Clemson, SC (US)

(*) Notice: Subject to any disclaimer, the term of this patent is extended or adjusted under 35 U.S.C. 154(b) by 0 days.

(21) Appl. No.: 14/844,654

(22) Filed: Sep. 3, 2015

(65) Prior Publication Data

US 2016/0046964 A1 Feb. 18, 2016

Related U.S. Application Data

(62) Division of application No. 12/615,558, filed on Nov. 10, 2009, now abandoned.

(60) Provisional application No. 61/114,574, filed on Nov. 14, 2008.

(51) Int. Cl.
*C12P 3/00* (2006.01)

(52) U.S. Cl.
CPC .................................. *C12P 3/00* (2013.01)

(58) Field of Classification Search
None
See application file for complete search history.

(56) References Cited

U.S. PATENT DOCUMENTS 5,807,722 A 9/1998 Gaddy
7,674,311 B2 3/2010 Gross et al.

OTHER PUBLICATIONS

Flythe et al. (Curr. Microbiol., vol. 61, pp. 125-131, 2010).*
Oyanedel et al. (J.Chem. Tech. &Biotech., vol. 80, pp. 206-215, 2005).*
Russell et al., "Enrichment and Isolation of a Ruminal Bacterium with a Very High Specific Activity of Ammonia Production," *Applied and Environmental Microbiology*, vol. 54, No. 4, Apr. 1988, pp. 872-877.
Chen et al., "Fermentation of Peptides and Amino Acids by a Monensin-Sensitive Ruminal Peptostreptococcus," *Applied and Environmental Microbiology*, vol. 54, No. 11, Nov. 1988, pp. 2742-2749.
Chen et al., "More Monensin-Sensitive, Ammonia-Producing Bacteria from the Rumen," *Applied and Environmental Microbiology*, vol. 55, No. 5, May 1989, pp. 1052-1057.
Paster et al., "Phylogeny of the Ammonia-Producing Ruminal Bacteria *Peptostreptococcus anaerobius*, *Clostridium sticklandii*, and *Clostridium aminophilum*," *International Journal of Systematic Bacteriology*, vol. 43, No. 1, Jan. 1993, pp. 107-110.
Whitehead et al., Abstract—"Isolation and Identification of Hyper-Ammonia Producing Bacteria from Swine Manure Storage Pits," *Current Microbiology*, Vo. 48, 2004, pp. 20-26.
Qureshi et al., Biofilm reactors for industrial bioconversion processes: employing potential of enhanced reaction rates; *Microbial Cell Factories*, 2050, vol. 4:24, pp. 1-21.
Du et al., A state of art review on microbial fuel cells: A promising technology for wastewater treatment and bioenergy; *Biotech. Adv.*, vol. 25 (2007), pp. 464-482.
Fantuzzi et al., An Electrochemical Microfluidic Platform for Human P450 Drug Metabolism Profiling *Anal. Chem.*, vol. 82, 2010, pp. 10222-10227.
Berge et al., In situ ammonia removal in bioreactor landfill leachate; *Waste Mgmt.*, vol. 26, 2006, pp. 334-343.
Mertoglu et al., Evaluation of in situ ammonia removal in an aerated landfill bioreactor; *Process Biochemistry*, vol. 41, 2006, pp. 2359-2366.
Percheron et al., Interactions between methanogenic and nitrate reducing bacteria during the anaerobic digestion of an industrial sulfate rich wastewater; *Fems Microbiol. Ecology*, vol. 29, 1999, pp. 341-350.
Apples et al., Principles and potential of the anaerobic digestion of waste-activated sludge; *Progress in Energy & Combustion Sci.*, vol. 34, 2008, pp. 755-781.
Chang et al., Biohydrogen production using an up-flow anaerobic sludge blanket reactor; *Intl. J. of Hydrogen Energy*, vol. 29, 2004, pp. 33-39.
Rychlik et al., Mathematical estimations of hyper-ammonia producing ruminal bacteria and evidence for bacteria antagonism that decreases ruminal ammonia production; *FEMS Microbiology Ecology*, vol. 32, 2000, pp. 121-128.
Kalala, dissertation; Development and testing of a bioreactor for production of hydrogen, pp. 1-81, 2007.
Negi et al., Optimization of Amylase and Protease Production from Aspergillus awamori in Single Bioreactor Through EVOP Factorial Design Technique; *Food Technol. Biotechnol.*, vol. 44 (2), pp. 257-261, 2006.
Oyanedel et al., Development of a membrane-assisted hybrid bioreactor for ammonia and COD removal in wastwateres; *J. Chem Technol. Biotechnol.*, vol. 80, pp. 206-215, 2005.

\* cited by examiner

*Primary Examiner* — Hope Robinson
(74) *Attorney, Agent, or Firm* — Dority & Manning, PA (57) ABSTRACT

Disclosed are methods for forming ammonia and ammonium that can be utilized in certifiably organic farming productions according to most if not all known certification standards. Also disclosed are bioreactors that can be utilized in carrying out disclosed methods. Methods and systems utilize obligate anaerobic bacteria to breakdown organic protein substrates, i.e., compounds containing bound nitrogen, to provide nitrogen in an unbound plant available form, and particularly, ammonia and/or ammonium. Obligate anaerobic bacteria include high ammonia producing bacteria such as *Peptostreptococcus anaerobius*, *Clostridium sticklandii*, and *Clostridium aminophilum*.

12 Claims, 6 Drawing Sheets

METHODS AND SYSTEMS FOR PRODUCTION OF ORGANICALLY DERIVED AMMONIA/AMMONIUM

CROSS REFERENCE TO RELATED APPLICATION

The present application is a divisional application of U.S. patent application Ser. No. 12/615,558, having a filing date of Nov. 10, 2009, now abandoned, and which claims filing benefit of U.S. Provisional Patent Application Ser. No. 61/114,574 having a filing date of Nov. 14, 2008, entitled "Methods and Systems For Production of Organically Derived Ammonia/Ammonium," both of which are incorporated herein by reference in their entirety.

BACKGROUND

Demand for organically produced produce has exploded over the past 20 years, with total U.S. organic sales expected to reach $20 billion in the current decade. Organic production methods are not only believed to provide produce containing higher nutritional quality than non-organically grown produce, due at least in part to a lack of industrial pesticides, herbicides, and the like being transmitted to the food; but are also believed to keep soils and local environments healthier, for instance due to a lack of industrial chemicals in runoff water.

In general, in order to be sold as organic, produce must be certified as such by a recognized governing board. While specific certification processes vary, requirements to obtain organic certification generally involve avoidance of the utilization of industrially produced chemicals on either the land or the produce. For instance, certified organic products utilized to provide nitrogen to the soil have in the past been limited to those in which the nitrogen remains chemically bound, generally in the form of amino acids, polypeptides, or complete proteins. As provided, this bound nitrogen is unavailable to plants. In order to be of use, the bound nitrogen must be converted to an available form through natural decomposition following application, which takes time and provides highly variable amounts of nitrogen. Conventional produce production, in contrast, has utilized industrially produced synthetic nitrogen in the form of ammonia/ammonium that is more readily available to plants as compared to bound nitrogen of organic fertilizers and can be applied in precise amounts at critical stages of plant development. Thus, the yield and characteristics of conventionally produced produce (e.g., size, color, etc.), can often outpace that of organically produced produce. However, methods for forming synthetic nitrogen species typically include conversion processes utilizing as starting materials nonrenewable resources such as natural gas, liquefied petroleum gas, or petroleum naphtha. Thus, utilization of synthetically-produced ammonia and/or ammonium is not conducive to organic production methods.

What are needed in the art are methods and systems for providing plant-available nitrogen to organic production methods. What are also needed in the art are environmentally friendly methods for producing ammonia and/or ammonium as may be used for any application, including organic farming methods.

SUMMARY

According to one embodiment, disclosed is a method for forming ammonia and/or ammonium. For instance, a method can include contacting a substrate with a hyper-ammonia producing obligate anaerobic bacteria, the contact taking place in a reduced salt solution and under anaerobic conditions. More specifically, the substrate can include bound nitrogen. A method can also include collecting the off-gases produced by the bacteria as the bacteria metabolizes the substrate, and separating ammonia and/or ammonium from the off-gasses.

Disclosed methods can be utilized for producing ammonia and/or ammonium for agricultural purposes, and in one particular embodiment, for organic agricultural purposes. In such an embodiment, the substrate can be an organic protein substrate.

Also disclosed herein is a bioreactor for producing ammonia and/or ammonium. A bioreactor can include, for example, a reaction chamber that is isolated from the atmosphere, a reduced salt solution contained in the reaction chamber, a substrate comprising bound nitrogen contained in the reaction chamber, and a hyper-ammonia producing obligate anaerobic bacteria.

A bioreactor can include additional components, for example one or more of an anaerobic reducing gas within which the salt is reduced, an anaerobic carrier gas for delivering the substrate, the salt, etc., to the bioreactor, and so forth.

The hyper-ammonia producing obligate anaerobic bacteria can be of a type that is naturally found in the rumen of an animal, for instance, *Peptostreptococcus anaerobius, Clostridium sticklandii, Clostridium aminophilum*, and combinations thereof.

The substrate can be an organic protein substrate, for instance soy protein isolate, blood meal, feather meal, fish meal, yeast extract, and combinations thereof.

Suitable salts can be, by way of example, $KH_2PO_4$, $Na_2SO_4$, $NaCl$, $MgSO_4 \cdot 7H_2O$, $CaCl_2 \cdot H_2O$, and mixtures thereof.

BRIEF DESCRIPTION OF THE FIGURES

The presently disclosed subject matter will become more fully understood from the detailed description and the accompanying drawings, wherein.

Repeat use of reference characters in the present specification and drawings is intended to represent the same or analogous features or elements of the present disclosure.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, disclosed herein are methods for forming ammonia and/or ammonium that need not utilize nonrenewable resources as starting or intermediate materials and do not require utilization of any synthetic or hazardous compounds (e.g., catalysts, etc.). Accordingly, produce farmed utilizing ammonia and/or ammonium formed according to disclosed methods can be certifiably organic according to most if not all known certification standards. Also disclosed herein are bioreactors that can be utilized in carrying out disclosed methods.

More specifically, disclosed methods and systems utilize certain obligate anaerobic bacteria to breakdown compounds containing bound nitrogen and provide nitrogen in an unbound plant-available form, and particularly, in the form of ammonia and/or ammonium.

It should be understood that disclosed methods can form both ammonia and ammonium. In general, a mixture of ammonia and ammonium can be formed, but the present disclosure is not limited to formation of a mixture of ammonia and ammonium. Moreover, a general reference to ammonia formation is intended to encompass both pure ammonia and an ammonia/ammonium mixture. As is known in the art, the relative proportion of ammonia to ammonium in a solution can depend upon solution characteristics and can be altered and controlled as desired.

Bacteria as may be utilized in disclosed methods can include any hyper-ammonia producing (HAP) obligate anaerobe. As utilized herein, the term "hyper-ammonia producing" generally refers to bacteria that can produce more than about 100 nmol $NH_3$/min/mg protein substrate, for instance more than about 200 nmol $NH_3$/min/mg protein substrate, or more than about 250 nmol $NH_3$/min/mg protein substrate in another embodiment. As utilized herein, the term HAP bacteria include HAP-like bacteria that differ genotypically from other, previously known HAP bacteria, but produce ammonia at levels as designated herein.

HAP bacteria have been found in the rumen of ruminant animals including but not limited to cattle, sheep, deer, goats etc. as well as in swine manure pits. Ammonia formation in the rumen by HAP bacteria is understood to be a major nutritional inefficiency in ruminant animals, wasting up to 25% of the protein provided in cattle and sheep diets, and is responsible for many of the odors emanating from anaerobic lagoons and swine production facilities. Accordingly, many in animal husbandry have searched for methods of inhibiting ammonia production by these bacteria. The presently disclosed subject matter, in contrast, takes advantage of the ammonia producing capabilities of these microorganisms.

While it is believed that many HAP bacteria have yet to be identified and classified, many have been isolated. For instance, *Peptostreptococcus anaerobius, Clostridium sticklandii*, and *Clostridium aminophilum* are three HAP bacteria isolated and identified in cattle rumen (see, e.g., Paster, et al., *International Journal of Systematic Bacteriology*, January 1993, p. 107-110), any of which can be incorporated into disclosed systems and methods. The disclosed methods are not limited to these particular HAP bacteria, however. For instance, several bacteria have been isolated from stored swine manure that produce ammonia at levels similar to those from cattle rumen that are phylogenetically distinct from the *P. anaerobius, C. sticklandii*, and *C. aminophilum* mentioned above (see, e.g., Whitehead, et al. *Current Microbiology*, 2004, V. 48, p. 20-26). These HAP bacteria could be used alternatively or in conjunction with other HAP bacteria.

In order to harness the ammonia and ammonium production capabilities of anaerobic HAP bacteria, and as obligate anaerobes have specific growth requirements, the present disclosure is directed in one embodiment to a bioreactor that can be used in carrying out disclosed production methods.

Figure 1:
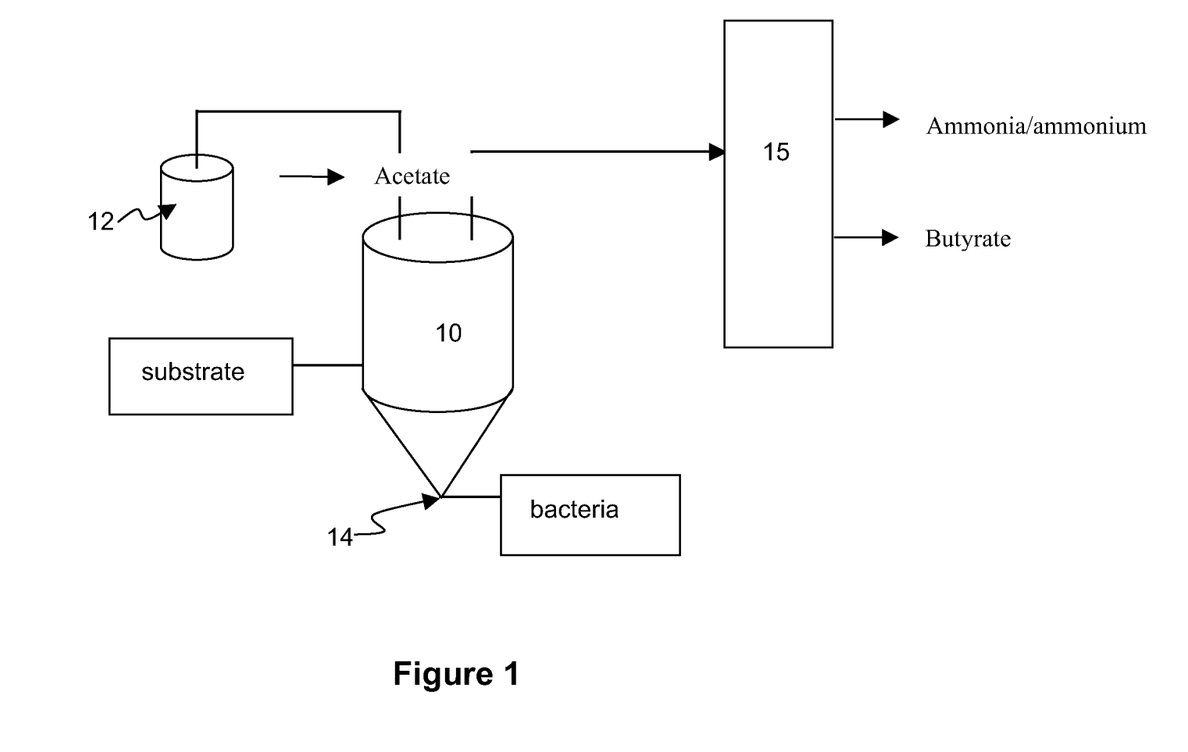
FIG. 1 is a schematic illustration of one embodiment of a bioreactor system as disclosed herein including a bioreactor 10, an electrochemical cell 12, and a fractional distillation column 15.

One embodiment of a bioreactor system is schematically illustrated in FIG. 1. A bioreactor system can include a bioreactor 10 capable of being isolated from the surrounding atmosphere. A bioreactor 10 can generally be formed of a material that can contain the bacteria and reactants of the ammonia production process at the desired conditions. For instance, a bioreactor can be stainless steel, borosilicate glass, Teflon® and other nonreactive temperature insensitive composite polymers, and so forth.

A bioreactor system can be run as a batch or continuous operation, as desired.

The bioreactor environment can include a buffering salt solution. Salts as may be utilized can include, without limitation, $KH_2PO_4$, $Na_2SO_4$, NaCl, $MgSO_4*7H_2O$, $CaCl_2*H_2O$, as well as mixtures of salts. A salt solution can be reduced under anaerobic conditions prior to combining with the HAP anaerobic bacteria according to any suitable reduction process. For example a salt solution can be reduced in an electrochemical cell 12 by gassing with any suitable anaerobic gas, e.g., carbon dioxide, hydrogen, nitrogen, mixtures thereof, or the like through the solution. The solution can be reduced to oxidation/reduction potential (OPR) of between about −100 mV and about −200 mV, for instance about 150 mV, in one embodiment.

Following reduction, the salt solution can be delivered to the bioreactor 10 from the electrochemical cell 12 by use of an anaerobic carrier gas. For instance, the same gas utilized during anaerobic reduction of the buffering salt solution or a different anaerobic gas can be used. In general, any purified anaerobic gas can be used to deliver the salt solution to the bioreactor 10. This can have the advantage of both delivering the reduced salt solution to the bioreactor 10 as well as purging any oxygen from the bioreactor during the delivery.

Also added to the bioreactor 10 can be a substrate for the HAP bacteria. In general, any substrate including bound nitrogen can be utilized. In those embodiments in which an ammonia/ammonium product for use in certified organic farming is desired, the substrate should also be material acceptable for organic practices. For example, organic protein substrates including, but not limited to, soy protein isolate (SPI), blood meal, feather meal, fish meal, yeast extracts, and so forth can be utilized, as well as combinations of substrates. A substrate can be added to a bioreactor before, during or after the loading of the reduced salt solution to the bioreactor. For instance, in one embodiment, a substrate can be added to a bioreactor prior to the sealing of the bioreactor 10 from the surrounding atmosphere. The reduced salt solution can then be delivered to the bioreactor using an anaerobic carrier and the bioreactor can be purged of oxygen and ready for inoculation with the HAP bacteria. In general the substrate can be added to the bioreactor in an amount of between about 0.1 g and about 1.6 g substrate to about 10 mL of salt solution. For instance between about 0.1 g and about 1.0 g substrate to about 10 mL salt solution.

Following preparation, the bacteria can be charged to the bioreactor 10 via an inoculation septum 14 and the culture can be allowed to develop. Preferred culture conditions can generally depend upon specific bacteria contained in the culture, but can generally include oxidation/reduction potential as outlined above, pH between about 6 and about 8, for instance between about 6.5 and about 7.5, temperature between about 35° C. and about 45° C., for instance about 40° C., pressure about ambient, and in general, the bacterial culture can be gently agitated, for instance through utilization of a stirring motor assembly operating at about 200 rpm.

The off gasses produced during the reaction process can include ammonia and ammonium in addition to other compounds. For instance, C. aminophilum produces ammonia and ammonium as well as butyrate and acetate. The off gasses can be separated following production to provide ammonia/ammonium for desired purposes according to any suitable separation process. For instance, in one embodiment, a fractional distillation column 15 can be used to separate the individual biodegradation components, e.g., acetate, butyrate, and ammonia/ammonium.

The materials produced by the process can be utilized in a variety of farming and/or industrial applications. For instance, in addition to utilization as an organic fertilizer (e.g., sold as an organic fertilizer, applied to fields in an organic farming operation, and so forth), ammonia/ammonium produced according to disclosed methods and processes can be utilized for applications including textile manufacturing, explosive manufacturing, and so forth.

The presently disclosed subject matter may be better understood with reference to the following examples.

EXAMPLE 1

Three different HAP bacteria were screened with five different organic protein sources to evaluate ammonia production.

Anaerobic gas utilized throughout the process included 10% carbon dioxide, 10% hydrogen and 80% nitrogen. To scrub out any oxygen contamination of the gasses, the gas was passed through a copper shaving filled borosilicate glass tube 1.5 meters in length, 1.5" in diameter and a thickness of 4 mm. This gas was passed from the bottom through to the top of the tube, The tube was wrapped with fiberglass shielded heating tape and heated to 300° C. Any oxygen contamination forms cupric oxide within the tube and the gas was completely anaerobic at this point. This gas is purified prior to ever entering any of the points into the system at any step.

Two salt solutions were prepared, an oxidation/reduction potential (ORP) color indication dye solution and a buffering solution. The salt solutions were prepared separately and then combined at specific times. The separate salt solutions were prepared as follows:

Salt A: (7.3 g $K_2HPO_4*3H_2O$/Liter of Distilled $H_2O$)
Salt B: (6.0 g $KH_2PO_4$, 12.9 g $Na_2SO_4$, 12.0 g NaCl, 2.5 g $MgSO_4*7H_2O$, 1.6 g $CaCl_2*H_2O$/L of Distilled $H_2O$).
ORP Indicator: Resazurin 0.0001 g/100 ml Distilled $H_2O$ 50 ml of Salt A and 50 ml of Salt B were added to a 1.5 L Erlenmeyer flask. The flask was topped with a butyl rubber stopper with two holes; one containing a ¼" stainless steel tube that extended to ½" from the bottom of the flask and to 2" above the stopper, This tube was used as the inlet tube for gas entry. A second tube extended 2" above and below the stopper for gas to escape from the flask. 850 ml distilled $H_2O$ and 1 ml of the Resazurin solution were added. The solution turned from clear to purple. This salt solution was then heated to boil point.

A buffering solution was formed including $Na_2CO_3$ 4 g/50 ml distilled $H_2O$. To form the solution, 4 g $Na_2CO_3$ was added to a 250 ml Erlenmeyer flask, 50 ml distilled $H_2O$ was then added and the flask was covered with aluminum foil. An 18 gauge anaerobic gas flushed syringe was inserted through the foil until the syringe touched the bottom of the flask. An anaerobic gas was bubbled through the solution as the solution was heated until beginning to boil. This buffering solution was transferred and combined with the ORP indicating solution using an anaerobic gas flushed pipette. Following combination, the buffered salt solution was heated to boiling and boiled for one minute. Following, 0.6 g of cysteine hydrochloride hepahydrate was added directly to the flask by cracking the stopper, upon which the solution turned bright pink.

This solution including the ORP indicating solution, the buffering solution and cysteine was immediately placed in an ice bath and continued to be gassed for 1 hour until the total solution turned clear.

After 1 hour of gassing the flask, 15 ml borosilicate septum test-tubes were prepared by adding the specific protein substrates and then gassed with anaerobic gas with an 18 gauge stainless steel needle as before to purge atmospheric oxygen from the test tubes and protein substrate. Following, 10 ml of the now reduced anaerobic salts solution was added via the pipette as be before. The pipette was removed while the needle was still purging atmospheric air from the test tube. A butyl rubber stopper was inserted simultaneously as the needle was removed, and an aluminum septum cap was mounted and crimped over the test-tube. Once all test-tubes were prepared, they were autoclaved for 20 minutes at 121° C. The test-tubes were removed from the autoclave, placed in an incubation chamber at 39° C. and allowed to equilibrate.

The test-tubes were inoculated with 0.5 ml of 18 hour mid-log phase bacterial inoculants using an anaerobically purged 21 gauge syringe needle. Specific inoculants and substrates for different tubes are shown on FIG. 2. The inoculated test-tubes were then placed back in the incubator.

Figure 2:
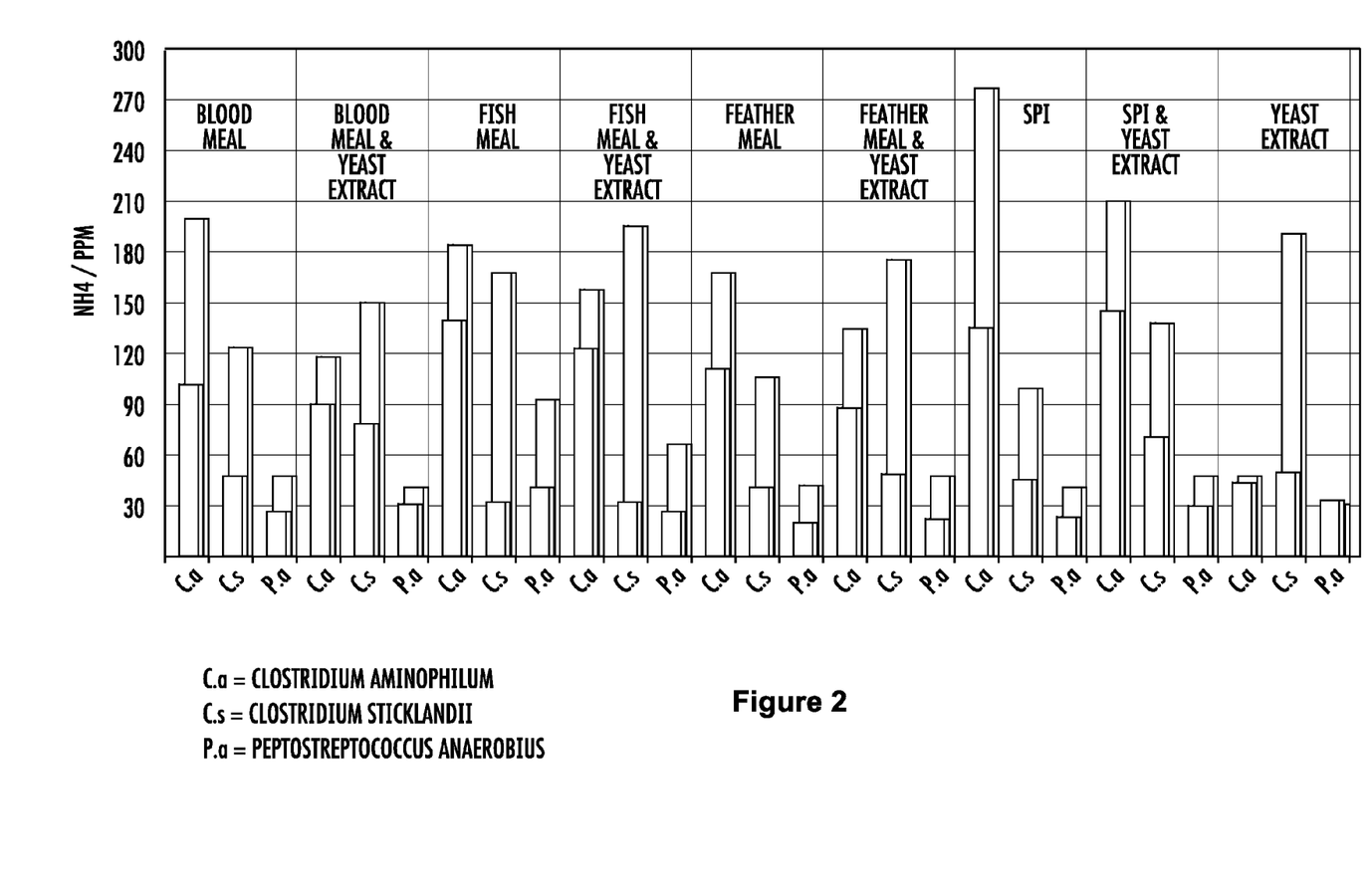
FIG. 2 illustrates the conversion of various organic protein sources to ammonia/ammonium by three different HAP bacteria and combinations thereof.

Results are shown in FIG. 2. Included in the results are ammonia/ammonium levels obtained at two different times, first at 48 hours (the smaller, front bars) and at 96 hours (the larger, back bars).

As can be seen, C. aminophilum produced more ammonia/ammonium than the other two HAP tested when cultured on a pure SPI substrate.

EXAMPLE 2

Figure 3:
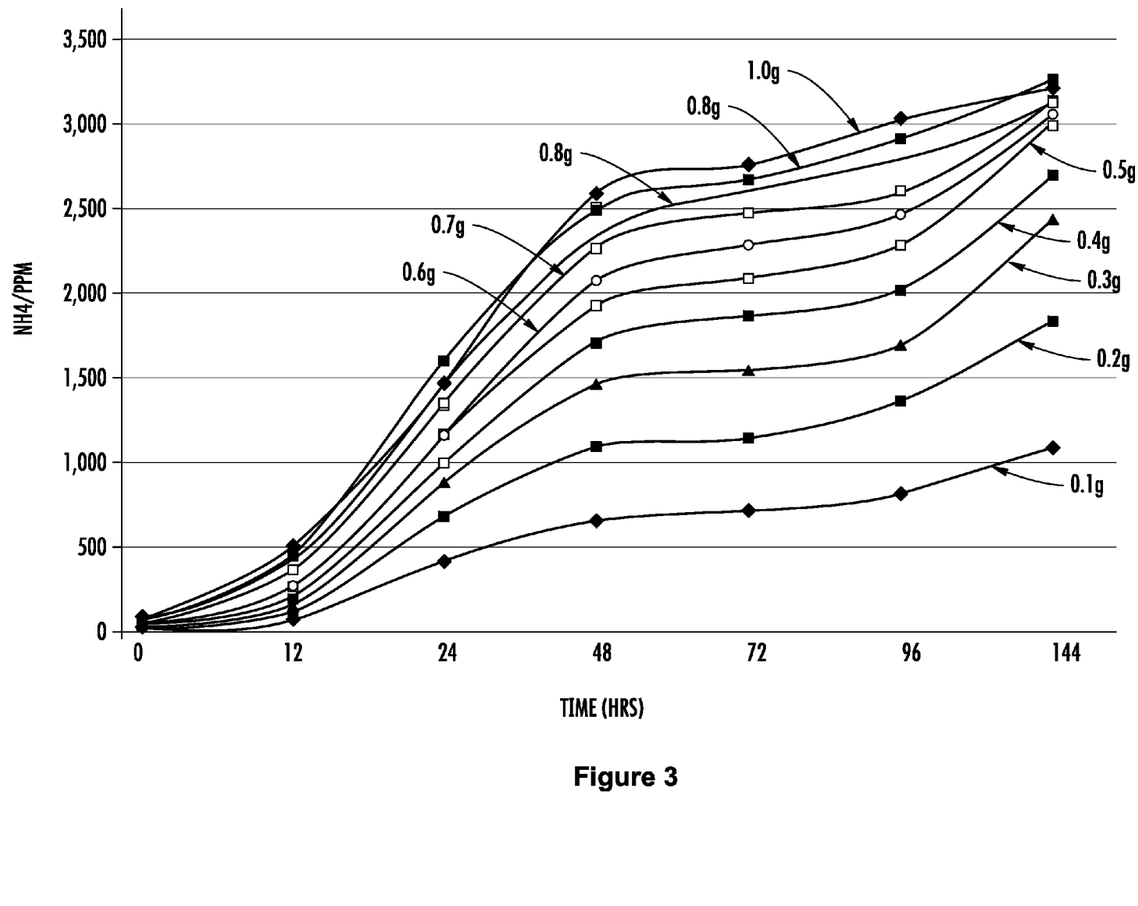
FIG. 3 graphically illustrates the conversion of soy protein isolate (SPI) at concentrations ranging between 0.1 g to 1.0 g to ammonia/ammonium by *Clostridium aminophilum* bacteria per 10 mL supporting salt solution.
Figure 4:
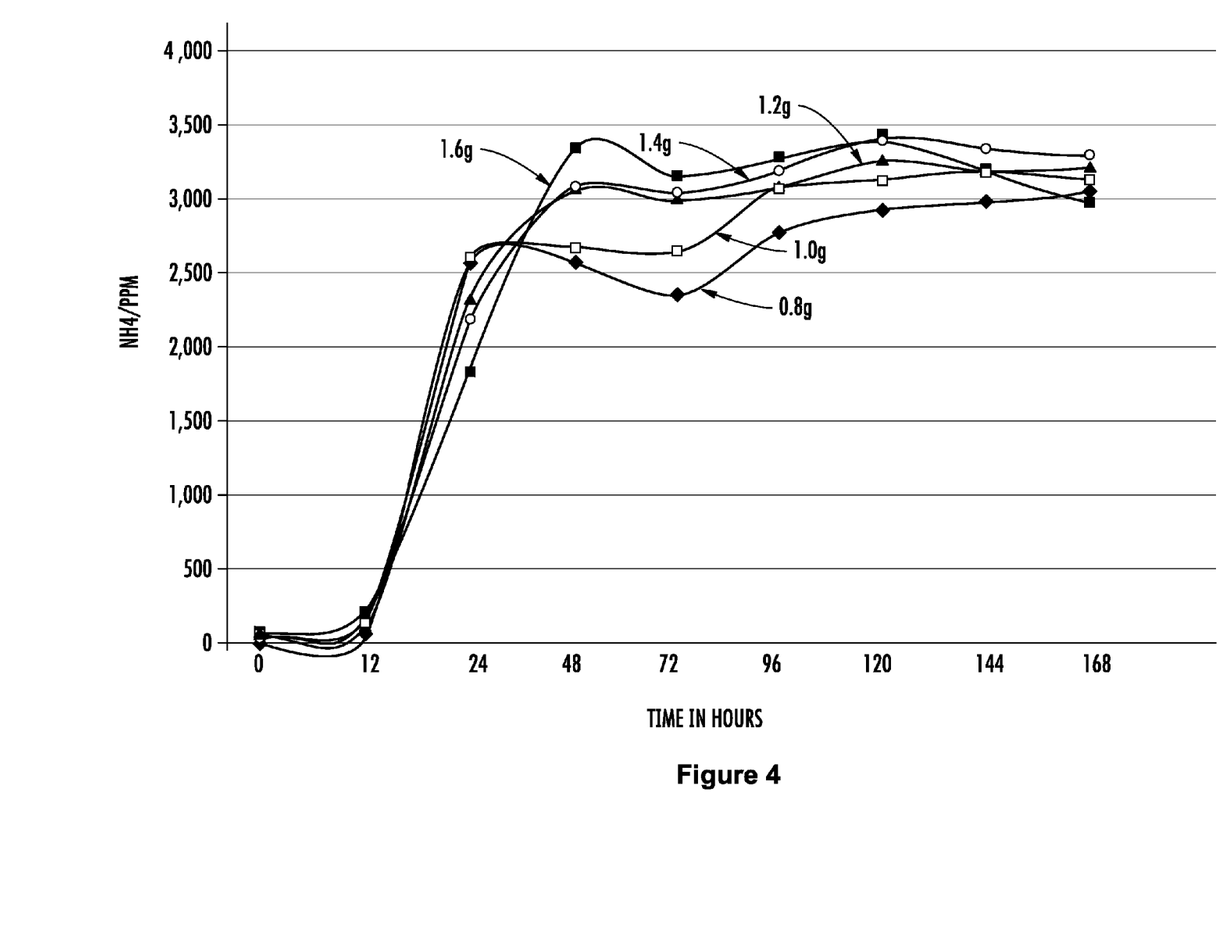
FIG. 4 graphically illustrates the conversion of soy protein isolate (SPI) at concentrations ranging between 0.8 g to 1.1.6 g to ammonia/ammonium by *Clostridium aminophilum* bacteria per 10 mL supporting salt solution.

Ammonia/ammonium production by C. aminophilum on a substrate of various concentration levels of SPI was examined using methodology as described above in Example 1. FIG. 3 shows results obtained over 144 hours for various SPI substrate concentration levels between 0.1 g per 10 mL of salt solution and 1.0 g per 10 mL of salt solution. FIG. 4 shows results obtained over 168 hours for various SPI substrate concentration levels from 0.8 g per 10 mL salt solution up to 1.6 g per 10 mL salt solution. Samples were taken every 24 hours as shown.

EXAMPLE 3

A large scale ammonia/ammonium production bioreactor was utilized to obtain organically produced material.

C. aminophilum was inoculated to a bioreactor with 1 kg SPI substrate at 110 ml bacteria (18 hr old in mid-log phase) per 10 L salt solution, The process used was chemically identical to that of the 10 ml test-tube examples described in Example 1 except instead of using a purged pipette to transfer the salt solution to the reactor, the air pressure from the gassing of the solution was used. The buffering solution was prepared in three 6 liter flasks, and the stoppers were equipped with two stainless steel tubes extending to the bottom. In addition, one of the tubes on each flask was closed with a clamp until the solution turned clear.

Following reduction of the buffering solution, the exhaust tube was clamped, the previously clamped tube was opened, and the pressure in the flask was used to force the reduced salt solution out of the now unclamped tube and into the bioreactor. The salt solution traveled by way of the butyl rubber tubing up and out of the flask over to the reactor. During such time as the flasks were being gassed and bubbled for an hour, 1 kg of SPI was added to the reactor, and the reactor including the substrate was gassed to purge the atmospheric oxygen from the inside of the reactor and the SPI.

When the salt solution was clear (anaerobic and ORP reduced to −150 mV), the solution was transferred as described without allowing any atmospheric oxygen to enter the system. A stirring motor was mounted to the top of the reactor lid. The stirring motor assembly was air-tight through the lid ball-bearing assembly with a stainless steel stirring propeller attached inside the reactor. The stirring motor was engaged after closing the reactor following the addition of the SPI and gassing started. Thus, the stirring motor was running prior to adding the salt solution.

Once the reactor was completely full of the SPI substrate and the reduced buffering solution, the anaerobic gas was shut off and the stirring motor turned off to the reactor. The reactor and all the contents were then autoclaved at 132° C. for 1 hour 51 minutes, The reactor was taken out of the autoclave, the stirring assembly turned back on and the temperature was allowed to cool to 39° C. at which point fiberglass sheathed heating tape that had been previously wrapped around the inverted cone portion of the reactor was turned on. A digital controller was utilized to maintain the internal reactor temperature at 39° C. Specifically, the digital controller included a stainless steel sensor that was inside the reactor attached through the lid with air-tight stainless steel hardware. The entire reactor was wrapped in aluminum backed fiberglass insulation to help maintain constant temperature.

100 ml of 18 hour mid-log phase bacteria were transferred through a butyl-rubber septum that was attached through the front of the reactor with stainless steel hardware with a 21 gauge sterile syringe needle that had been purged with anaerobic gas. Prior to inoculation, a multi-parameter sensor/sonde was calibrated and sterilized in ethanol, and anaerobic gas was turned on to create a positive pressure inside the reactor. A portal previously capped was uncapped and various sensors inserted into the port. There was a thick butyl rubber gasket that surrounded the sensor that was pushed securely into the portal, creating an air-tight fit. Once the sensor was inside the reactor and was actively recording, the anaerobic gas flow was again turned off. At this point the reactor was inoculated.

Figure 5:
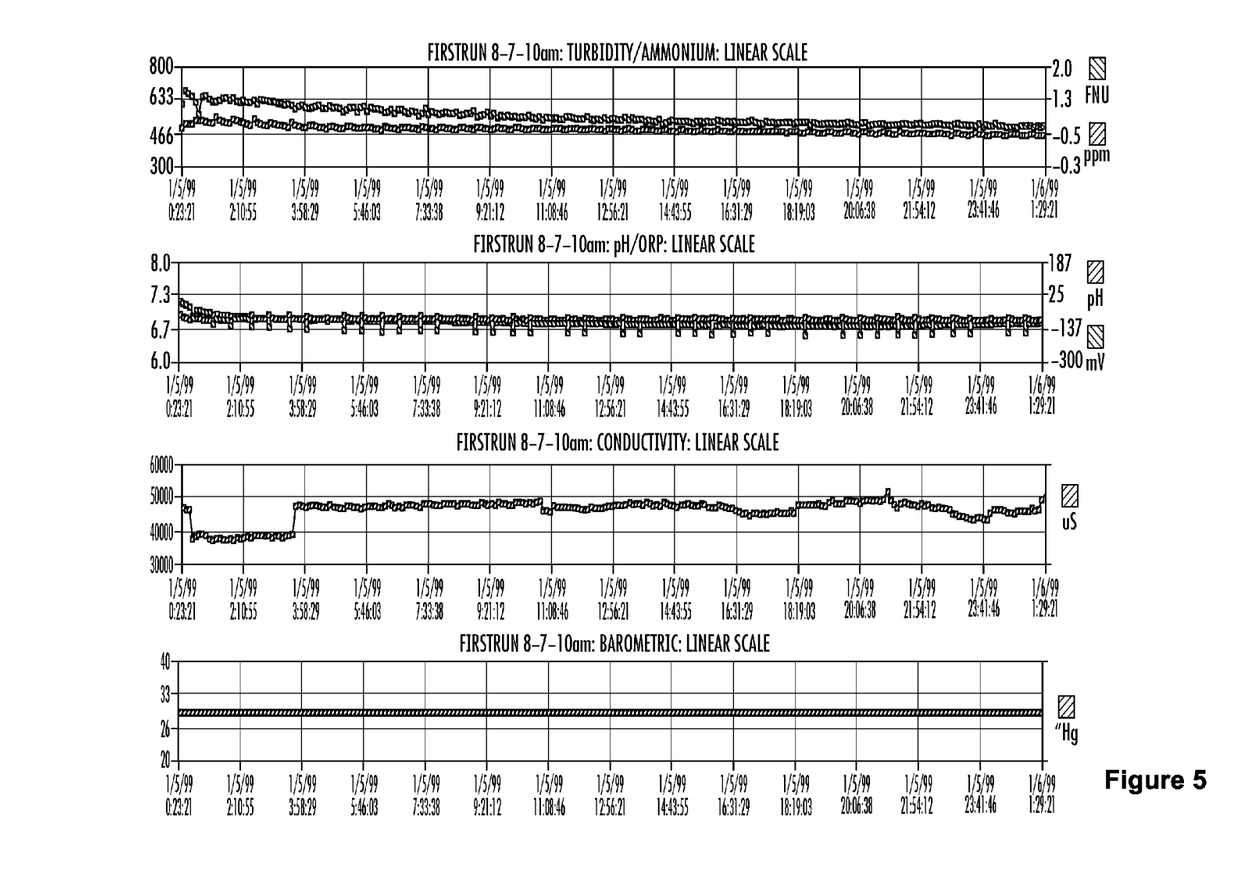
FIG. 5 illustrates various parameters examined during an ammonium production process as described herein.
Figure 6:
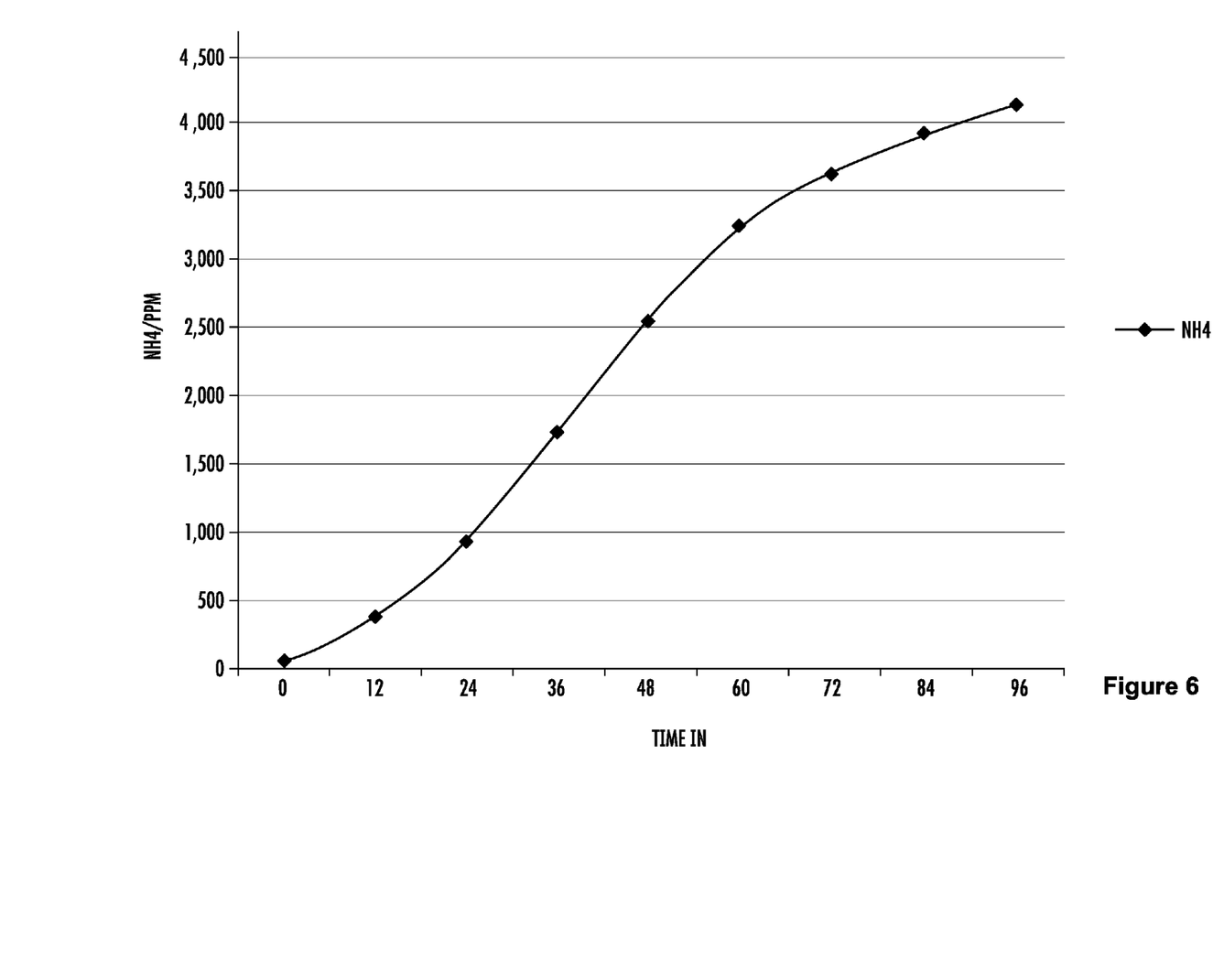
FIG. 6 graphically illustrates results of an ammonium production process as described herein.

FIG. 5 provides an example of several parameters of a production process followed over the course of the experimental run including turbidity/ammonium, pH, conductivity, and barometric pressure. FIG. 6 provides the ammonium production over time for the first 96 hours of production time. Conditions throughout the culture were maintained as follows: pH 6.74, temperature 39° C., stirring speed 200 rpm, and pressure ambient barometric pressure.

FIG. 6 illustrates ammonium production obtained over a 96 hour culture period.

It will be readily understood by those persons skilled in the art that the present disclosure is susceptible of broad utility and application. Many embodiments and adaptations of the present disclosure other than those herein described, as well as many variations, modifications and equivalent arrangements, will be apparent from or reasonably suggested by the present disclosure and the foregoing description thereof, without departing from the substance or scope of the presently disclosed subject matter. Accordingly, while the present subject matter has been described herein in detail in relation to described embodiments, it is to be understood that this disclosure is only illustrative and exemplary of the present subject matter and is made merely for purposes of providing a full and enabling disclosure. The foregoing description is not intended or to be construed to limit the presently disclosed subject matter or otherwise to exclude any such other embodiments, adaptations, variations, modifications and equivalent arrangements.

What is claimed is:

1. A method for producing ammonia and/or ammonium, comprising:
    contacting a substrate with a hyper-ammonia producing obligate anaerobic bacteria, wherein the contacting is in a reduced salt solution formed with an anaerobic gas in an electrochemical cell and under anaerobic conditions, wherein the substrate comprises nitrogen;
    collecting off-gases produced by the bacteria as the bacteria metabolizes the substrate; and
    separating the ammonia and/or ammonium from the off-gasses, wherein the substrate comprises soy protein isolate, blood meal, feather meal, fish meal, yeast extract, or combinations thereof, and wherein the hyper-ammonia producing obligate anaerobic bacteria is selected from the group consisting of *Peptostreptococcus anaerobius*, *Clostridium sticklandii*, *Clostridium aminophilum*, and combinations thereof.

2. The method of claim 1, further comprising utilizing the ammonia and/or ammonium for agricultural purposes.

3. The method according to claim 2, wherein the agricultural purposes are organic agricultural purposes.

4. The method of claim 1, wherein the salt solution is reduced in oxidation/reduction potential to a potential of between −100 mV and −200 mV.

5. The method of claim 1, wherein the substrate contacts the hyper-ammonia producing obligate anaerobic bacteria at a pH of between 6 and 8.

6. The method according to claim 1, wherein the substrate contacts the hyper-ammonia producing obligate anaerobic bacteria at a temperature of between 35° C. and 45° C.

7. The method according to claim 1, further comprising agitating the solution as the substrate contacts the hyper-ammonia producing obligate anaerobic bacteria.

8. The method of claim 1, wherein the substrate is an organic protein substrate comprising nitrogen.

9. The method according to claim 1, wherein the hyper-ammonia producing obligate anaerobic bacteria is a type of bacteria naturally found in the rumen of an animal.

10. The method of claim 1, wherein the ammonia and/or ammonium are separated from the off-gasses with a fractional distillation process.

11. The method according to claim 1, wherein the salt of the reduced salt solution comprises $KH_2PO_4$, $Na_2SO_4$, NaCl, $MgSO_4*7H_2O$, $CaCl_2*H_2O$, or mixtures thereof.

12. The method of claim 1, wherein the substrate is carried to the reduced salt solution with an anaerobic carrier gas.

* * * * *